(12) United States Patent
Hargreaves

(10) Patent No.: US 7,534,563 B2
(45) Date of Patent: May 19, 2009

(54) METHODS FOR PRODUCING LIGAND ARRAYS

(75) Inventor: John S. Hargreaves, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 553 days.

(21) Appl. No.: 10/610,829

(22) Filed: Jun. 30, 2003

(65) Prior Publication Data

US 2004/0265476 A1 Dec. 30, 2004

(51) Int. Cl.
*C12Q 1/68* (2006.01)

(52) U.S. Cl. ............................... 435/6; 506/7; 428/405

(58) Field of Classification Search ....................... None
See application file for complete search history.

(56) References Cited

U.S. PATENT DOCUMENTS

| | | | |
|---|---|---|---|
| 6,171,797 B1 * | 1/2001 | Perbost ........................ | 435/6 |
| 6,258,454 B1 * | 7/2001 | Lefkowitz et al. ........... | 428/333 |
| 6,291,183 B1 * | 9/2001 | Pirrung et al. ................ | 435/6 |
| 6,319,674 B1 | 11/2001 | Fulcrand et al. | |
| 6,344,316 B1 * | 2/2002 | Lockhart et al. ............. | 435/6 |
| 6,387,631 B1 | 5/2002 | Arnold et al. | |
| 6,444,318 B1 * | 9/2002 | Guire et al. .................. | 428/412 |
| 2007/0218373 A1 * | 9/2007 | Ito et al. ....................... | 430/5 |

OTHER PUBLICATIONS

Nivens et al., Book of Abstracts, 217 ACS National Meeting, Anaheim, California, 1999.*
Conrad et al., Proceedings of SPIE-The International Society for Optical Engineering 2978:12-21, (1997).*

* cited by examiner

*Primary Examiner*—Christopher Low
*Assistant Examiner*—Jeffrey S. Lundgren

(57) ABSTRACT

Methods for producing ligand substrates and arrays, e.g., peptide and nucleic acid arrays, as well as the arrays produced thereby, methods for use of the arrays and kits that include the same are provided. In the subject methods, a substrate having a surface displaying photocleavable functional groups that produce surface bound photocleavage produced functional groups upon irradiation is first provided, where the photocleavable groups are then cleaved to produce a surface that displays desired functional groups. The resultant substrates, optionally after an additional functionalization step, are then contacted with ligands or monomeric precursors thereof, e.g., via deposition of each different ligand onto a different region of the surface, resulting in covalent attachment of the contacted ligands to the surface. The subject methods find use in the preparation of a variety of different types of arrays, where the produced arrays find use in a variety of different applications, including both genomic and proteomic applications.

20 Claims, 1 Drawing Sheet

METHODS FOR PRODUCING LIGAND ARRAYS

INTRODUCTION

1. Technical Field

The field of this invention is ligand arrays, including protein and nucleic acid arrays.

2. Background of the Invention

Arrays of binding agents (ligands), such as nucleic acids and polypeptides, have become an increasingly important tool in the biotechnology industry and related fields. These binding agent or ligand arrays, in which a plurality of binding agents are positioned on a solid support surface in the form of an array or pattern, find use in a variety of applications, including gene expression analysis, drug screening, nucleic acid sequencing, mutation analysis, and the like.

A feature of many arrays that have been developed is that each of the polymeric compounds of the array is stably attached to a discrete location on the array surface, such that its position remains constant and known throughout the use of the array. Stable attachment is achieved in a number of different ways, including covalent bonding of the polymer to the support surface and non-covalent interaction of the polymer with the surface.

Where the ligands of the arrays are polymeric, e.g., as is the case with nucleic acid and polypeptide arrays, there are two main ways of producing such arrays, i.e., via in-situ synthesis in which the polymeric ligand is grown on the surface of the substrate in a step-wise fashion and via deposition of the full ligand, e.g., a presynthesized nucleic acid/polypeptide, cDNA fragment, etc., onto the surface of the array.

In certain fabrication protocols currently employed, the substrate surface is functionalized to display hydroxyl groups at some point in the fabrication protocol. As such, a number of different protocols for producing hydroxyl group functionalized substrates have been developed. However, there is continued interest in the development of new protocols for producing hydroxyl group functionalized substrate surfaces.

3. Relevant Literature

U.S. Pat. Nos. 6,319,674; 6,291,183; 6,258,454; 6,387,631B1 and references cited therein.

SUMMARY OF THE INVENTION

Methods for producing surface modified substrates and ligand arrays, e.g., peptide and nucleic acid arrays, as well as the substrates and arrays produced thereby, methods for use of the substrates and arrays and kits that include the same are provided. In the subject methods, a substrate that has a surface displaying photocleavable functional groups that produce surface bound functional groups, e.g., hydroxyl functional groups, upon irradiation is first provided. The photocleavable groups are then cleaved, e.g., via irradiation, to produce a surface that displays the desired functional groups. The resultant substrates, optionally after an additional functionalization step(s), may then contacted with reagents, e.g., monomeric residues or premade ligands thereof, e.g., via deposition of each different reagent onto a different region of the surface, resulting in covalent attachment of the ligands to the surface. The subject methods find use in the preparation of a variety of different types of arrays, where the produced arrays find use in a variety of different applications, including both genomic and proteomic applications.

DEFINITIONS

Figure 1:
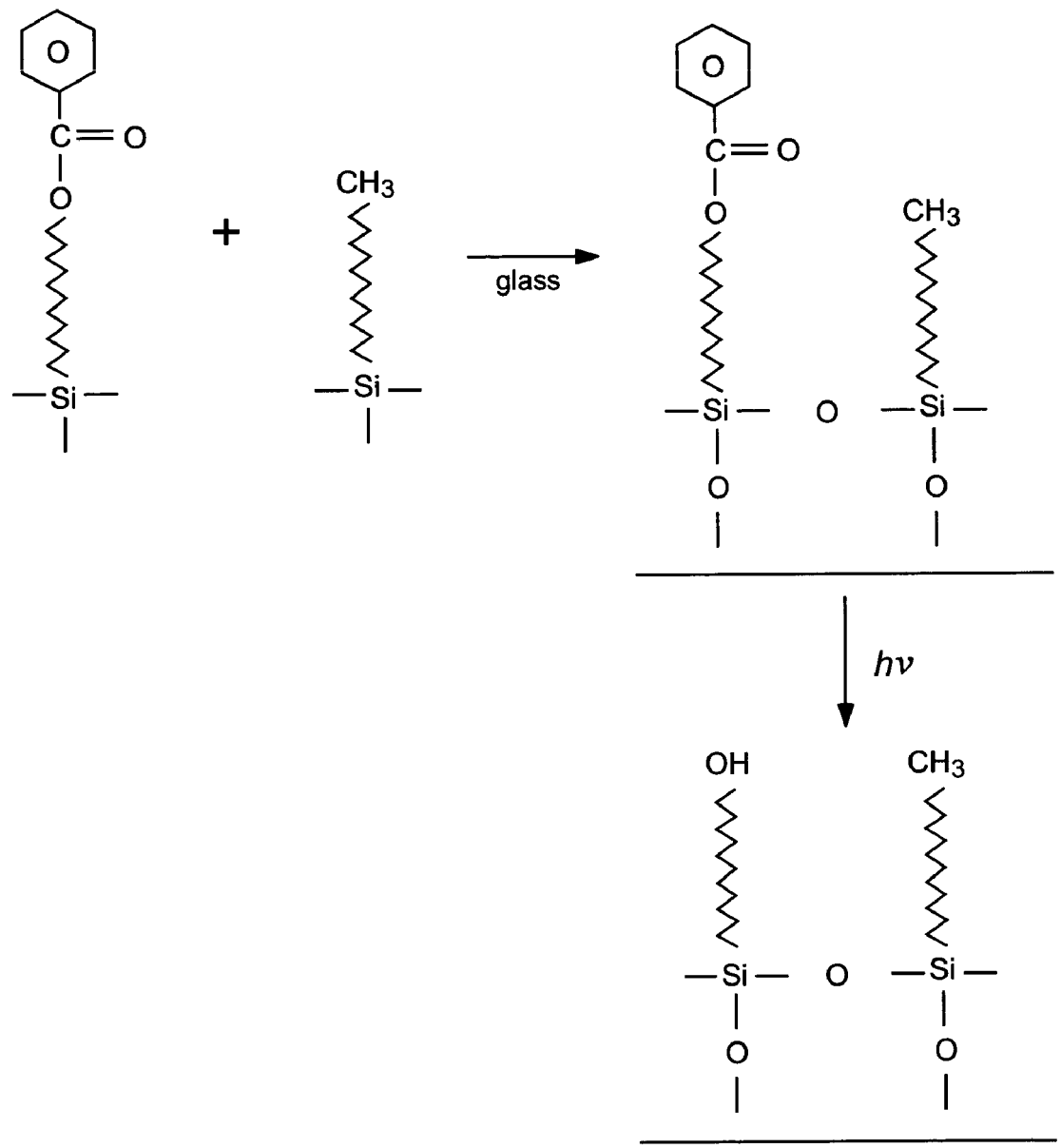
FIG. 1 provides a schematic representation of a surface derivatization protocol according to the subject invention.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "peptide" as used herein refers to any polymer compound produced by amide formation between an α-carboxyl group of one amino acid and an α-amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single-stranded nucleotide multimers of from about 10 to about 100 nucleotides and up to 200 nucleotides in length.

The term "polynucleotide" as used herein refers to single- or double-stranded polymers composed of nucleotide monomers of generally greater than about 100 nucleotides in length.

The term "functionalization" as used herein relates to modification of a solid substrate to provide a plurality of functional groups on the substrate surface. By a "functionalized surface" as used herein is meant a substrate surface that has been modified so that a plurality of functional groups are present thereon.

The term "array" encompasses the term "microarray" and refers to an ordered array presented for binding to ligands such as polymers, polynucleotides, peptide nucleic acids and the like.

The terms "reactive site", "reactive functional group" or "reactive group" refer to moieties on a monomer, polymer or substrate surface that may be used as the starting point in a synthetic organic process. This is contrasted to "inert" hydrophilic groups that could also be present on a substrate surface, e.g., hydrophilic sites associated with polyethylene glycol, a polyamide or the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2-50 monomers, preferably about 2-20, more preferably about 3-10 monomers.

The term "ligand" as used herein refers to a moiety that is capable of covalently or otherwise chemically binding a compound of interest. The arrays of solid-supported ligands produced by the methods can be used in screening or separation processes, or the like, to bind a component of interest in a sample. The term "ligand" in the context of the invention may or may not be an "oligomer" as defined above. However, the term "ligand" as used herein may also refer to a compound that is "pre-synthesized" or obtained commercially, and then attached to the substrate.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like.

The term "alkyl" as used herein refers to substituted or unsubstituted, cyclic, or linear, branched or unbranched saturated hydrocarbon group of 1 to 24 carbon atoms. Examples include methyl, ethyl, n-propyl, isopropyl, n-butyl, isobutyl, t-butyl, octyl, decyl, tetradecyl, hexadecyl, eicosyl, tetracosyl and the like, 3-methyl-octyl, 3-methoxy-octyl, 3-chloro-octyl and the like, as well as cycloalkyl groups such as cyclopentyl, cyclohexyl and the like.

The term "alkenyl" as used herein refers to substituted or unsubstituted, cyclic, or linear, branched or unbranched unsaturated hydrocarbon group of 1 to 24 carbon atoms. Examples include octenyl, nonenyl, decenyl, undecenyl and the like, isopropenyl, isobutenyl, isopentenyl, octenyl, isoprenyl and the like.

The term "alkoxy" as used herein refers to a substituent —O—R wherein R is alkyl as defined above. Examples of alkoxy groups include methoxy, ethoxy, n-propoxy, isopropoxy, sec-butoxy, tert-butoxy and the like.

The terms "halogen" or "halo" are used to refer to a chloro, bromo, fluoro or iodo substituent, or combinations thereof, such as dichloro, chlorobromo, dichlorobromo and the like.

A "silane" or "silanizing reagent" refers to a compound or reagent in which a central silicon atom is bonded to four substituents, wherein the substituents may be the same or different.

The term "protecting group" refers to chemical moieties that, while stable to the reaction conditions, mask or prevent a reactive group from participating in a chemical reaction. Protecting groups may also alter the physical properties such as the solubility of compounds, so as to enable the compounds to participate in a chemical reaction. Examples of protecting groups are known in the art, for example, Greene et al., *Protective Groups in Organic Synthesis*, 2nd Ed., New York: John Wiley & Sons, 1991.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

An "array," includes any one-dimensional, two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulsejets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171, 797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioned on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

DESCRIPTION OF THE SPECIFIC EMBODIMENTS

Methods for producing ligand arrays, e.g., peptide and nucleic acid arrays, as well as the arrays produced thereby, methods for use of the arrays and kits that include the same are provided. In the subject methods, a substrate having a surface displaying photocleavable functional groups that produce surface bound hydroxyl functional groups upon irradiation is first provided. The photocleavable groups are then cleaved to produce a surface that displays hydroxyl functional groups. The resultant substrates, optionally after an additional functionalization step(s), are then contacted with ligands or monomeric precursors thereof, e.g., via deposition of each different ligand onto a different region of the surface, resulting in covalent attachment of the contacted ligands to the surface. The subject methods find use in the preparation of a variety of different types of arrays, where the produced arrays find use in a variety of different applications, including both genomic and proteomic applications.

Before the invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components which are described in the publications which might be used in connection with the presently described invention.

Methods

As summarized above, the invention provides methods for producing a substrate, as well as an array of at least two different ligands covalently bonded to a surface of the substrate. The subject methods include providing a substrate having a surface displaying photocleavable functional groups. The photocleavable functional groups of the provided surface-functionalized substrates are then converted to desired reactive functional groups, e.g., hydroxyl functional groups, e.g., via irradiation of the surface at an appropriate wavelength. In certain embodiments, the methods are performed in manner that produces a pattern-functionalized surface. Following the conversion step, (and optionally a further functionalization step) ligands may be produced on the substrate surface, e.g., by contacting the substrate surface with ligands or precursors thereof so as to produce a ligand array. Each of these steps is now described in greater detail below.

Substrates

In the subject methods, the first step is to provide a substrate having a surface that displays photocleavable functional groups, e.g., that can be photocleaved to produce hydroxyl functional groups. While such a substrate may be provided using any convenient protocol, in one representative embodiment the surface of a solid substrate is first contacted with a derivatizing composition that contains one or more types of silanes, where the one or more types of silanes includes a photocleavable group-functionalized silane. As such, in one embodiment the derivatizing composition is made up of a single type of silanizing agent, while in another embodiment, the derivatizing composition includes at least two different silanes or silanizing reagents, one of which is the photocleavable group functionalized silane. The surface of the solid substrate is contacted with the one or more silanes under reaction conditions effective to couple the silanes to the substrate surface via reactive hydrophilic moieties present on the substrate surface, where the derivatizing composition may be contacted with the substrate surface in a fluid or gaseous (i.e., vapor) phase. The reactive hydrophilic moieties on the substrate surface include substituted or unsubstituted hydroxyl, carboxyl, aldehyde, thiol, amino groups or combinations of hydrophilic moieties, or hydrophilic groups masked by a protecting group that may be removed to provide reactive hydrophilic moieties.

The substrate may be made of any material that has a plurality of reactive hydrophilic sites on its surface, or that can be treated or coated so as to have a plurality of such sites on its surface. Suitable materials include, but are not limited to, glass (particularly controlled pore glass, or "CPG"), quartz, silicon or silicon covered with silicon dioxide, ceramics, supports typically used for solid phase chemical synthesis, e.g., cross-linked polymeric materials (e.g., divinylbenzene styrene-based polymers), agarose (e.g., SEPHAROSE™), dextran (e.g., SEPHADEX™), cellulosic polymers, polyacrylamides, and the like. The supports may be obtained commercially and used as is, or they may be treated or coated prior to functionalization. The substrate surfaces are typically planar, although planarity is not required and the surfaces can be of any geometry suitable for contact with silanizing reagents used in formation of an array.

In some embodiments, the substrate surface is "cleaned/primed" prior to contact with the silanizing reagent of one or more silane(s). In certain of these embodiments, the surfaces may be placed in contact with a solvent prior to contact with the silanizing reagents. The solvent, prepared prior to contact with the surfaces, may be generated by dissolution of a small amount of water in a hydrophobic solvent, such as toluene, benzene and the like. The surfaces may be first placed in contact with the solvent, followed by the addition of the silanizing reagents.

The substrate surfaces are derivatized by contact with one or more silanizing reagents to produce functionalized surfaces. A variety of silanizing reagents may be used. It is known in the art of silane chemistry that substituents that are facile leaving groups on the silane facilitate binding of the silane to hydrophilic moieties on substrate surfaces are of interest. Examples of leaving group substituents on the silane include, but are not limited to: halogens, alkoxy, aryloxy moieties, and the like. Hydrophilic moieties, for example hydroxyl groups, react with silanes, displacing the leaving group on the silane to form a siloxy bond to the substrate surface.

As described in greater detail below, the derivatizing composition made up of one or more silanizing reagents that is contacted with the substrate may be contacted with the substrate in either a fluid or vapor phase. As such, in certain embodiments where the derivatizing composition is a fluid, the silanizing reagents are contacted with the surface of the substrate in the presence of a sufficient amount of water and/or other solvent to provide for the silylation reaction. In yet other embodiments, a vapor phase of the silanizing reagents is contacted with the substrate surface.

The subject methods may be employed to produce a variety of functionalized surfaces for use in polymer arrays, depending on the silanizing reagent used and the derivation chemistry, as described in more detail below.

Preparation of Photocleavable Group Functionalized Substrate Surfaces

The derivatizing composition comprises at least one type of silane, where the silane includes a photocleavable functional group. In many embodiments, the derivatizing composition may include two types of silanes, a first silane that may be represented as $R^1$—$Si(R^L R^x R^y)$ and a second silane having the formula: $Y\text{-}(L)_n\text{-}Si(R^L R^x R^y)$. In these formulae, the $R^L$, which may be the same or different, are leaving groups; the $R^x$ and $R^y$, which may be the same or different, are either lower alkyl or leaving groups like $R^L$. $R^1$ is a chemically inert moiety that upon binding to the substrate surface lowers the surface energy thereof; n is 0 or 1, L is a linking group, and Y is the photocleavable functional group as summarized above and described in greater detail below.

In those embodiments where the surface is contacted with only a single type of silane, the silane is the photocleavable group functionalized silane described above. Reaction of the substrate surface with the derivatizing composition is carried out under reaction conditions effective to couple the silane(s) to the surface hydrophilic moieties and thereby provide —Si-$(L)_n$-Y groups, and —Si—$R^1$ groups and depending on the embodiment, on the substrate surface.

More specifically, the $R^L$ moieties, which are leaving groups, are such that they enable binding of the silanes to the surface. Typically, the leaving groups are hydrolyzable so as to form a silanol linkage to surface hydroxyl groups. Examples of suitable leaving groups include, but are not limited to, halogen atoms, particularly chloro, and alkoxy moieties, particularly lower alkoxy moieties. The $R^x$ and $R^y$ are either lower alkyl, e.g., methyl, ethyl, isopropyl, n-propyl, t-butyl, or the like, or leaving groups as just described with respect to $R^L$. Thus, each type of silane will generally contain a trichlorosilyl functionality, a tri(alkoxysilyl) functionality, wherein the alkoxysilyl is a lower alkoxysilyl group such as trimethoxysilyl, triethoxysilyl, etc., mixed functionalities such as diisopropylchlorosilyl, dimethylchlorosilyl, ethyldichlorosilyl, methylethylchlorosilyl and the like.

In those embodiments where a mixture of silanes make up the derivatizing composition, the first silane is a derivatizing agent that reduces surface energy as desired, while the second silane provides the photocleavable functionality. Thus, with respect to the first silane, coupling to the substrate yields surface —Si—$R^1$ groups as explained above, wherein $R^1$ is a chemically inert moiety that upon binding to the substrate surface lowers surface energy. By "chemically inert" is meant that $R^1$ will not be cleaved or modified when the functionalized substrate is used for its intended purpose, e.g., in solid phase chemical synthesis, hybridization assays, or the like. Typically, $R^1$ is an alkyl group, generally although not necessarily containing in the range of 2 to 24 carbon atoms, such as in the range of 4-10 to 18 carbon atoms.

The second silane, upon coupling, provides surface —Si-$(L)_n$-Y moiety groups, where Y is the photocleavable functionality. Of course, if the $R^x$ and $R^y$ are not leaving groups, the surface moieties provided will actually be —Si$R^xR^y$-$(L)_n$-Y moiety groups, which applicants intend to encompass by the more generic representation —Si-$(L)_n$-Y moiety. The "Y" or photocleavable moiety is any moiety that, upon irradiation of light at an appropriate wavelength for a given duration, is cleaved from the remainder of the silanizing reagent to produce a terminal desired functional group, e.g., a terminal hydroxyl group. Typically, the photocleavable group is a group that is cleaved upon irradiation by light of a wavelength ranging from about 230 to 700 nm, such as from about 230 to about 500 nm, for a duration of about 0.01 to about 10 s, such as from about 0.01 to about 1 s. In certain embodiments, the photocleavable group is one that has an absorption coefficient of from about 5000 to about 100,000, such as from about 5000 to about 50,000. In certain embodiments, the photocleavable group is one that has quantum yield of reaction ranging from about 0.01 to about 1, such as from about 0.01 to about 0.5 (as determined by actinometry, where specifically the number of hydroxyl groups formed per unit time (e.g., seconds) is measured, e.g., by reacting the hydroxyl groups with a functionalized dye, such as CY3, and measuring the absorption spectrum of the dye).

In certain embodiments, the photocleavable moiety or group is chosen from amide, carbonyl, ester, peroxide and aromatic derivatives thereof. In certain embodiments, the photocleable moiety is an aromatic-oxy group. A specific photocleavable moiety or group of interest is benzoyloxy.

L represents a linker and n is 0 or 1, such that a linker may or may not be present. If a linker is present, it will generally be a $C_1$-$C_{24}$ hydrocarbon linnking group. Normally, L is $C_1$-$C_{24}$ alkyl, such as $C_2$-$C_{18}$ alkyl, including $C_3$-$C_{18}$ alkyl.

The density of the photocleavable functional groups on the substrate surface, following reaction with the derivatizing composition, is determined by the relative proportions of the first and second silanes in the derivatizing composition. That is, a higher proportion of the second silane in the derivatizing composition will provide a greater density of alkenyl function groups, while a higher proportion of the first silane will give rise to a lower density of alkenyl groups. Optimally, the first silane is present in the range of approximately 0 wt. % to 99.5 wt. % of the derivatization composition, such as in the range of approximately 20 wt. % to 90 wt. % of the composition, while the second silane correspondingly is present in the range of approximately 0.5 wt. % to 100 wt. % of the derivatization composition, such as in the range of approximately 10% wt. % to 80 wt. % of the composition, where about a 1:1 ratio of first to second silanizing reagents is of interest in certain embodiments.

In certain embodiments, the resultant surface of the functionalized substrates contains both —Si—$R^1$ and Si-$(L)_n$-Y functional groups, present at a predetermined ratio, with the ratio determining both surface energy and density of functional groups. In other words, the functional surface of the substrate displays photocleavable functional groups. See also U.S. Pat. No. 6,258,454 for a further description of the general process of derivatizing a surface, the disclosure of which is herein incorporated by reference.

As indicated above, the derivatizing composition made up of one or more silanizing reagents is contacted with the substrate under conditions sufficient for the silanizing agent(s) to covalently bond to the substrate surface. Contact may be conducted in either a fluid or a vapor phase, such that the derivatizing compositions may be a fluid or vapor when it is contacted with the substrate surface. As such, in certain embodiments where the derivatizing composition is a fluid, contact occurs in a fluid phase. In yet other embodiments, a vapor phase of the silanizing reagents is contacted with the substrate surface. Each of these representative embodiments is now further described separately.

Where the derivatizing composition is contacted with the substrate surface in a fluid phase, the derivatizing composition typically is made up of the one or more silanizing agents present in a suitable solvent or solvents, where the solvents may be aqueous or organic, and the solvent component may or may not include both an aqueous component and an organic component. Aqueous solvents of interest include, but are not limited to: pure water, water having one or more dissolved components, e.g., salts, etc. and the like. Organic solvents of interest include, but are not limited to: benzene, toluene, ethanol, methanol and the like.

In an alternative embodiment, the derivatizing composition is contacted with the array surface in a gaseous or vapor phase. The vapor phase derivatizing composition may be contacted with the surface, or introduced to the surface, at low pressure, atmospheric pressure, among others. The temperature may be below room temperature, room temperature or above room temperature. For example, contact of the vapor phase at a higher than room temperature and low pressure may be employed in certain embodiments. The use of such vapor phase derivatizing compositions allows for ease in processing.

Derivatization of the surface according to these embodiments may be carried out in a directional stream of derivatizing composition at low pressure. Low-pressure derivatization occurs by first placing the substrate into a vacuum chamber, such as an extremely low pressure vacuum chamber. The derivatizing composition is then bled into the vacuum chamber at a selected rate to promote directionality of the derivatizing composition stream. Preferably, the vacuum chamber includes pressures ranging from about $10^{-5}$ torr to about 1 torr to promote the directionality of the stream.

In certain embodiments, the derivatization steps occur at atmospheric pressure. At atmospheric pressure, the substrate is held over a solution of derivatizing composition at atmospheric pressure, such as at room temperature, or at a temperature ranging from about 10° C. to about 50° C., including at about 20° C. The substrate may be held over the derivatizing composition for about 10 minutes or less. The derivatizing composition can also be blown against the substrate surface by way of forced convection and the like, and even mixed with a water vapor, a carrier gas, or the like.

An advantage of the vapor phase contact of the derivatizing composition with the substrate surface, even at atmospheric pressure, is simplicity of the protocol and lack of need for use of solvents.

Conversion of Photocleavable Functional Groups to Hydroxyl Functional Groups

The resultant surfaces displaying photocleavable functional groups are then typically further derivatized to produce surfaces displaying desired functional groups, e.g., hydroxyl functional groups. As such, the next step in the subject methods is to convert the photocleavable functional groups on the substrate surface as described above to the desired functional groups. The photocleavable functional groups are converted to desired functional groups using any convenient protocol, e.g., via irradiation at an appropriate wavelength for a sufficient period of time. While the particular results achieved may vary, the percentage of initial photocleavable functional groups that are converted is, in many embodiments, at least about 5%, usually at least about 10% and more usually at least about 20% of the initial number of photocleavable functional groups, where the number % may be higher, e.g., 30, 40, 50, 60, 70, 80, 90, 95, 99.

As indicated above, the next step in the subject invention is to irradiate the substrate surface with light of a sufficient wavelength for a sufficient period of time to cleave the photocleavable groups from the surface and produce the desired functional groups. Typically, the surface is irradiated with light ranging in wavelength from about 230 nm to about 700 nm, such as from about 230 to about 350 nm, for a period of time ranging from about 0.1 s to about 60 s, such as from about 1 s to about 10 s. Light of suitable wavelength may be provided using any convenient means, e.g., mercury lamp, flash photolysis, laser and the like.

The above photocleavage or irradiation protocols result in conversion of the photocleavable functional groups to desired, e.g., hydroxyl, functional groups, and specifically cleavage of the terminal photocleavable groups which results in the production of terminal desired functional groups.

Patterned Functionalized Substrate Surface

In certain embodiments, the above method is performed in a manner that produces a patterned functionalized substrate surface, and more specifically a patterned hydroxyl group functionalized substrate surface. By "patterned hydroxyl group functionalized substrate surface" is meant a surface in which the photocleavage resultant, e.g., hydroxyl, functionalities are located on the surface in a predetermined pattern, i.e., a defined collection of regions. In other words, the desired functionalities are not randomly distributed across the substrate surface, but are instead located in predetermined regions or locations on the substrate surface.

The patterned functionalized surfaces of these embodiments can be produced using any convenient protocol or approach. For example, the entire surface may be initially functionalized with photocleavable groups, and the groups then selectively cleaved in defined regions of the surface to produce the desired functionalized pattern. For example, the entire substrate surface may be contacted as described above with a homogenous or heterogeneous composition of the photocleavable group containing silanizing agent, and the resultant modified surface selectively exposed to light of suitable wavelength and duration to cleave the photocleavable groups in the desired areas or regions, e.g., with a laser raster scanned over the surface or with a light directed through a mask, to produce the desired patterned functionalized surface.

Instead of using a selective irradiation source, e.g., a laser, as described above, a photoresist layer that includes the desired pattern may be produced on top of the photocleavable group functionalized surface, where the pattern photoresist layer modified surface is then exposed to irradiation followed by removal of the photoresist layer to produce the desired patterned functionalized surface. For example, a suitable patterned photoresist material may be produced on the initially photocleavable group functionalized surface by first coating the surface with the photoresist material and then exposing the photoresist coating to light through a mask to produce the desired patterned photoresist layer. The resultant surface is then blanket exposed to light of appropriate wavelength and duration to remove the photocleavable groups in the exposed regions, followed by removal of the photoresist layer to produce the desired pattern functionalized surface. Suitable photoresist materials, masks and methods for use of the same are well known to those of skill in the art, where any of a variety of currently known materials and methods for their use may be employed in the subject invention, as will be readily apparent to those of skill in the art.

Alternatively, only certain regions or portions of the surface may be initially functionalized with the photocleavable moiety functionalized silanizing agent. In other words, the photocleavable silanizing agent in the initial surface functionalization step of the subject methods is contacted with the substrate surface in only those regions/locations/areas where a hydroxyl functionality is ultimately desired. Described another way, the substrate surface is selectively functionalized with the photocleavable moiety prior to the irradiation step. The surface of the substrate may be selectively functionalized with a photocleavable group or moiety using any convenient protocol. For example, a patterned photoresist layer may be first produced on the substrate surface, e.g., with a mask as described above. The resultant patterned photoresist layer modified surface may then be contacted with a photocleavable group functionalized silanizing agent, as described above, such that the surface is selectively functionalized with the photocleavable silanizing agent. The photoresist layer may then be removed, and the entire surface contacted with a non-photocleavable group silanizing agent, e.g., a second silanizing agent as described above. The resultant surface is then exposed to light of sufficient wavelength for a sufficient duration to produce the desired patterned functionalized surface.

It should be noted that the above specific protocols for producing a patterned functionalized surface are merely representative, and in no way limiting on the subject invention. Other approaches for producing patterned surfaces are readily determinable and come within the scope of the invention.

Ligand Attachment

The resultant functionalized surface may be used immediately for covalent ligand (or precursor thereof) attachment or, where desired, further functionalized prior to ligand (or precursor thereof) attachment. For example, in many embodiments the ligand to be covalently attached to the surface may be functionalized with an amino functional group, which provides for covalent attachment of the ligand to the substrate surface via reaction of the ligand functional group with the surface hydroxyl functional group.

Alternatively, the functional, e.g., hydroxyl, group may be converted to a number of different types of functional groups which are reactive to the ligand (or precursor thereof) of interest, i.e., ligand reactive functional groups. By ligand reactive functional groups is meant groups that react with moieties present on the target ligands, (i.e., the ligands to be deposited onto the surface and covalently bound thereto) in a manner that produces a covalent bond or linkage between the ligand and the substrate surface. The functional, e.g., hydroxyl, functional groups may be converted to a variety of different types of reactive moieties using a variety of different protocols, depending on the particular nature of the ligand that is to be covalently bound to the substrate surface. Where the functional group is a hydroxyl functional group, representative ligand reactive functional groups to which the initial hydroxyl functional groups may be converted include: aldehydes, amines, and the like. The particular ligand reactive functional group to which the initial functional group is converted will be chosen, at least in part, on considerations that include, but are not limited to: the nature of the ligand and functional groups that may be present thereon, ease of conversion, and the like.

The particular conversion protocol employed will vary with respect to the nature of the desired ligand reactive functional group, and may or may not involve the production of one or more intermediate groups. In one embodiment, the hydroxyl functional groups of the initial substrate surface are converted to aldehyde functional groups, e.g., via controlled oxidation to aldehyde functionalities, e.g., via Moffat oxidations, where primary alcohols are specifically and efficiently converted to the corresponding aldehydes under mild conditions. See e.g., Pftizner and Moffatt, Comp. Org Syn. 7, 291 (1991), J. Amer. Chem. Soc. (1965) 87:5670-78. In yet another embodiment, the surface hydroxyl groups are converted to amine reactive benzaldehyde functionalities using benzaldehyde phosphoramidites. More specifically, the hydroxyl moiety can be reacted with a benzaldehyde phosphoramidite, followed by acidic deprotection of the benzaldehyde moiety and basic deprotection of the phosphate moiety. Such protocols are known in the art, see e.g., WO 01/09385 and its priority application Ser. No. 09/364,320, the disclosure of latter of which is herein incorporated by reference.

Following production of the desired, e.g., hydroxyl, functional groups, and any subsequent functionalization of the hydroxyl groups, as described above, the resultant functionalized surface can be employed in the fabrication of arrays, e.g., via polymeric ligand deposition where one or more polymeric ligands are contacted with the functionalized surface; or in-situ polymeric ligand synthesis, as described immediately below in greater detail.

Features of the Functionalized Substrate Surfaces

A feature of the functionalized surfaces produced according to the subject invention is that they are particularly suitable for use as substrates in ligand array production. In certain embodiments, the functionalized surfaces are characterized by being functionalized according to a pattern, as described above.

Polymeric Ligand Attachment in Array Fabrication

In many embodiments, the subject surfaces prepared as described above are employed in array facbrication where polymeric ligands are attached to the surface. In these embodiments, the ligands that are contacted with the substrate surface are typically polymeric binding agents. The polymeric binding agents may vary widely, where the only limitation is that the polymeric binding agents are made up of two more, usually a plurality of, monomeric units covalently attached in sequential order to one another such that the polymeric compound has a sequence of monomeric units. Typically, the polymeric binding agent includes at least 5 monomeric units, usually at least 10 monomeric units and more usually at least 15 monomeric units, where in many embodiments the number of monomeric units in the polymers may be as high as 5000 or higher, but generally will not exceed about 2000. In certain embodiments, the number of monomeric residues in the polymeric binding agent is at least about 50, usually at least about 100 and more usually at least about 150.

Polymeric binding agents of particular interest include biopolymeric molecules, such as polypeptides, nucleic acids, polysaccharides and the like, where polypeptides and nucleic acids, as well as synthetic mimetics thereof, are of particular interest in many embodiments.

In many embodiments, the polymeric binding agents are nucleic acids, including DNA, RNA, nucleic acids of one or more synthetic or non-naturally occurring nucleotides, and the like. The nucleic acids may be oligonucleotides, polynucleotides, including cDNAs, mRNAs, peptide-nucleic acids and the like. Where the polymeric compounds are nucleic acids, the nucleic acids will generally be at least about 5 nt, usually at least about 10 nt and more usually at least about 15 nt in length, where the nucleic acids may be as long as 5000 nt or longer, but generally will not exceed about 3000 nt in length and usually will not exceed about 2000 nt in length. In many embodiments, the nucleic acids are at least about 25 nt in length, usually at least about 50 nt in length and may be at least about 100 nt in length.

The polymers are characterized by having a functional moiety that reacts with the ligand reactive functional moiety present on the substrate surface to produce a covalent bond between the ligand and the substrate surface. The ligand may naturally include the desired reactive functionality, or may be modified to include the desired reaction functionality. Representative reactive functionalities of interest include, but are not limited to: amine groups, hydroxyl groups, sulfhydryl, phosphoramidite, anhydrides, and the like.

The polymers employed in the methods may be prepared using any convenient methodology. The particular means of preparing the polymer to include the requisite reactive group where it is not initially present will depend on the nature of the polymer and the nature of the reactive group that is to be incorporated into the polymer.

As mentioned above, in practicing the methods, typically at least two distinct polymers are contacted with the substrate surface that bears the reactive ligand functionalities. By distinct is meant that the two polymers differ from each other in terms of sequence of monomeric units. The number of different polymers that are contacted with the substrate surface may vary depending on the desired nature of the array to be produced, i.e. the desired density of polymeric structures. Generally, the number of distinct polymers that are contacted with the surface of the array will be at least about 5, usually at least about 10 and more usually at least about 100, where the number may be as high as 1,000,000 or higher, but in many embodiments will not exceed about 500,000 and in certain embodiments will not exceed about 100,000.

The polymers are generally contacted with the surface in an aqueous solvent, such that aqueous conditions are established at the surface location to which the polymer is to be covalently attached. The temperature during contact typically ranges from about 10 to about 60 and usually from about 20 to about 40° C. Following initial contact, the aqueous solution of polymer is typically maintained for a period of time sufficient for the desired amount of reaction to occur, where the period of time is typically at least about 20 sec, usually at least about 1 min and more usually at least about 10 min, where the period of time may be as great as 20 min or greater.

Each polymer is typically contacted with the substrate surface as part of an aqueous composition, i.e. an aqueous composition of the polymer in an aqueous solvent is contacted with the surface of the array. The aqueous solvent may be either water alone or water in combination with a co-solvent, e.g. an organic solvent, and the like. The aqueous composition may also contain one or more additional agents, including: acetic acid, monochloro acetic acid, dichloro acetic acid, trichloro acetic acid, acetonitrile, catalysts, e.g. lanthanide (III) trifluoromethylsulfate, lithium chloride, buffering agents, e.g. sodium phosphate, salts, metal cations, surfactants, enzymes, etc.

The aqueous polymer composition may be contacted with the surface using any convenient protocol. Generally, the aqueous polymer composition is contacted with the surface by depositing the aqueous polymer composition on the surface of the substrate. The aqueous volume may be deposited manually, e.g. via pipette, or through the use of an automated machine or device. A number of devices and protocols have been developed for depositing aqueous solutions onto precise locations of a support surface and may be employed in the present methods. Such devices include "pulse-jet" printing devices, mechanical deposition or pipetting devices and the like. See e.g. U.S. Pat. Nos. 4,877,745; 5,338,688; 5,474,796; 5,449,754; 5,658,802; 5,700,637; and 5,807,552; the disclosures of which are herein incorporated by reference. Robotic devices for precisely depositing aqueous volumes onto discrete locations of a support surface, i.e. arrayers, are also commercially available from a number of vendors, including: Genetic Microsystems; Cartesian Technologies; Beecher Instruments; Genomic Solutions; and BioRobotics, to name representative vendors.

The amount of fluid that is deposited may vary. For example, volumes ranging from about 1 nl to 1 pl, usually from about 60 to 100 nl may be deposited onto the substrate surface. Following contact and incubation for a period of time and under conditions sufficient for the desired reaction to occur, as described above, the surface of the resultant array may be further processed as desired in order to prepare the array for use, as described below. As such, the array surface may be washed to remove unbound reagent, e.g., unreacted polymer, and the like. Any convenient wash solution and protocol may be employed, e.g., flowing an aqueous wash solution, e.g., water, methanol, acetonitrile, and the like, across the surface of the array, etc. The surface may also be dried and stored for subsequent use, etc.

The above-described protocols for array fabrication can be carried out using the devices described in U.S. Pat. Nos. 6,242,266; 6,232,072 and 6,180,351; the disclosures of which are herein incorporated by reference.

In-Situ Synthesis in Array Fabrication

As indicated above, the substrate surfaces displaying hydroxyl functional groups can also be employed in in-situ ligand synthesis applications. The in-situ synthesis methods include those described in U.S. Pat. No. 5,449,754 for synthesizing peptide arrays, as well as WO 98/41531 and the references cited therein for synthesizing polynucleotides (specifically, DNA) using phosphoramidite or other chemistry. Further details of in situ methods are provided in U.S. Pat. Nos. 6,242,266, 6,232,072, 6,180,351, 6,171,797, 6,323,043, and U.S. patent application Ser. No. 09/302,898 all referenced above. Such in-situ synthesis methods can be regarded as iterating the sequence of depositing: (a) a protected monomer onto predetermined locations on a substrate to link with either a suitably activated substrate surface (or with a previously deposited deprotected monomer); (b) deprotecting the deposited monomer so that it can now react with a subsequently deposited protected monomer; and (c) depositing another protected monomer for linking. Different monomers may be deposited at different regions on the substrate during any one cycle so that the different regions of the completed array will carry the different biopolymer sequences as desired in the completed array. One or more intermediate further steps may be required in each iteration, such as oxidation and washing steps. The substrate surfaces may also be employed in the well-known light directed in-situ polymeric array synthesis protocols.

The above described pattern functionalized surfaces find particular use in in situ array synthesis protocols, e.g., in the production of high resolution arrays via in situ synthesis production methods. Such arrays are described in greater detail below.

The above protocol produces ligand arrays that can be employed in a variety of different applications, as described in greater detail below.

Whether the ligands are deposited onto the surface of the array in premade form or produced on the surface in situ by deposition of precursors thereof, a common step to both approaches is the production of the desired two or more ligands on the photocleaved functionalized surface. A feature of certain embodiments is that two or more different ligands or precursors thereof are deposited (e.g., by pulse-jet deposition) onto discrete regions or domains of the photocleaved functionalized surface following a given photocleavage step and prior to any additional photocleavage step. In other words, in any embodiments where two or more cycles are practiced as defined by two or more photocleavage steps, two or more ligands (or precursors thereof) are deposited in any given cycle, i.e., between photocleavage steps. In certain embodiments, the subject methods are characterized by including a single photocleavage step that occurs prior to deposition of any ligands or precursors thereof.

Arrays

The invention also provides arrays of polymeric binding agents produced according to the methods described above. The arrays include at least two distinct polymers that differ by monomeric sequence immobilized on, e.g., covalently bonded to, different and known locations on the substrate surface. In certain embodiments, each distinct polymeric sequence of the array is typically present as a composition of multiple copies of the polymer on the substrate surface, e.g., as a spot on the surface of the substrate. The number of distinct polymeric sequences, and hence spots or similar structures, present on the array may vary, but is generally at least 2, usually at least 5 and more usually at least 10, where the number of different spots on the array may be as a high as 50, 100, 500, 1000, 10,000 or higher, depending on the intended use of the array. The spots of distinct polymers present on the array surface are generally present as a pattern, where the pattern may be in the form of organized rows and columns of spots, e.g., a grid of spots, across the substrate surface, a series of curvilinear rows across the substrate surface, e.g., a series of concentric circles or semi-circles of spots, and the like. The density of spots present on the array surface may vary, but will generally be at least about 10 and usually at least about 100 spots/cm$^2$, where the density may be as high as 10$^6$ or higher, but will generally not exceed about 10$^5$ spots/cm$^2$. In other embodiments, the polymeric sequences are not arranged in the form of distinct spots, but may be positioned on the surface such that there is substantially no space separating one polymer sequence/feature from another.

In the broadest sense, the arrays of the invention are arrays of polymeric binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini e.g., the 3' or 5' terminus. In other embodiments, the arrays are arrays of polypeptides, e.g., proteins or fragments thereof.

In certain embodiments, the arrays produced according to the subject methods are in situ produced high resolution arrays, where by high resolution is meant that the density of the individual features have a high density. By high density is meant at least about 100 features/cm$^2$, usually at least about 500 features/cm$^2$, where the density may, in certain embodiments, range from about 500 to about 10,000 or more, such as from about 500 to about 10,000 features/cm$^2$. This high resolution feature is achievable using in situ preparation protocols particular in those embodiments where the substrate surface is a pattern functionalized surface, as described above.

Utility

The arrays find use in a variety of different applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g., an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in: U.S. Pat. Nos. 4,591,570; 5,171,695; 5,436,170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

In certain embodiments, the methods include a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in using an array made by the method of the present invention, the array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER scanner available from Agilent Technologies, Palo Alto, Calif. Other suitable apparatus and methods are described in U.S. Pat. Nos. 5,091,652; 5,260, 578; 5,296,700; 5,324,633; 5,585,639; 5,760,951; 5,763,870; 6,084,991; 6,222,664; 6,284,465; 6,371,370 6,320,196 and 6,355,934; the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

Kits

Kits for use in analyte detection assays are also provided. The kits at least include the arrays of the invention. The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the array assay devices for carrying out an array based assay. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette.

The following examples are offered by way of illustration and not by way of limitation.

EXAMPLES

Preparation of Hydroxyl Group Functionalized Surface

A. Glass slides were derivatized with a monolayer of benzoyloxypropyltrimethoxysilane in the following manner:

Water was dissolved in toluene by vigorous stirring overnight such that the final concentration of water was about 250 to 350 µg/ml. Glass slides were then placed in this solvent. To one liter of this solvent was added approximately 16 mls of benzoyloxypropyltrimethoxysilane. The solution was stirred for about 2 hours at room temperature, after which the slides were removed and rinsed with (1) toluene, (2) methanol and finally (3) water. The slides were then air-dried.

The contact angle for the surface was observed to be approximately 67 degrees.

For contact angle determination, approximately 25 µl of water was dropped onto the derivatized surface. The contact angle was measured with a FTA (First Ten Angstroms) 200 goniometer with software provided by Accusoft Corp.

The slides were then irradiated at either 248 nm or 365 nm with a low-pressure mercury lamp for approximately 12 hours.

The contact angle for the surface after photolysis was observed to be approximately 37 degrees. This lowering of the contact angle is due to the cleavage of the benzoyloxy group to produce the more hydrophilic hydroxyl group.

If this surface is treated with a solution of decyltrichlorosilane in toluene the contact angle of the photolyzed surface increases from about 37 degrees to about 100 degrees. This result shows that the trichlorosilane groups have reacted with the hydroxyl groups generated by the photolysis to form a hydrophobic layer with aliphatic groups now being at the surface of the layer.

This increase in contact angle does not occur if the surface is not irradiated. This is easily proved by exposing the surface on the glass slide to light of 254 nm. Since the glass acts a filter to light of this wavelength the surface on the reverse of the slide will not be irradiated. The contact angle of the reverse side after treatment with decyltrichlorosilane is much lower than the contact angle on the obverse, irradiated, side of the slide.

B. Further proof of the concept can be seen from surfaces prepared using a mixture of silanating reagents, for instance a mixture of benzoyloxypropyltrimethoxysilane with decyltrichlorosilane for 2 hours at room temperature in a manner described above and schematically shown in FIG. 1. The contact angle of a film made from a mixture of benzoyloxytripropyltrimethoxysilane and decyltrichlorosilane in the ratio of 1:0.05 to 0.20 is about 95 degrees before photolysis and about 40 degrees after photolysis. The change in contact angle for this system is much higher than the change observed for the surface containing only the photcleavable silane.

Mixed layers using aliphatic trichlorosilanes ranging from, for instance, $C_4$ to $C_{10}$, can also be used to produce surfaces of high contact angle of about 95 degrees. This achievement is despite the expectation that the much more reactive trichlorosilanes might derivatize the surface to the exclusion of the much less reactive trimethoxysilane. This high contact angle is required if the surfaces are to be written with a writer using the ink-jet principle.

C. Further proof of the concept can be seen by irradiating the surface through a reticle or mask with defined areas, such as small circles of approximately 2 mm in diameter, with light of a specific wavelength. Such an approach produces a patterned functionalized surface, as described above. After irradiation, treatment of the surface with a fluorescent dye solution such as CY3, which specifically attaches to the hydroxyl groups, shows well-defined areas that fluoresce.

D. Further proof of the concept can be shown by substituting the photocleavable benzolyoxy group with a chromophore that has a much lower absorption coefficient and a lower quantum yield of photocleavage. For instance the contact angle of a surface prepared exclusively from 11-trichloroundecylsilane acetate is about 67 degrees before photolysis and about 67 degrees after photolysis, showing that very little, if any, hydrophilic hydroxy groups have been produced.

It is evident from the above results and discussion that an important new protocol for preparing polymeric arrays, particularly nucleic acid arrays, is provided by the subject invention. The methods for modification of the substrate surfaces are safe and readily provide functionalized surfaces that retain a high contact angle, thereby providing desirable spotting properties on the array. Additionally, arrays produced from the subject modified substrates exhibit low background signals and low non-specific target binding. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing an array of at least two different ligands covalently bonded to a surface of a substrate, said method comprising:
   (a) providing a substrate having a surface displaying photocleavable functional groups by contacting a surface of a substrate with a first silanizing reagent comprising a terminal photocleavable functional group to produce a surface displaying photocleavable functional groups;
   (b) cleaving said photocleavable functional groups on said surface to produce a patterned surface displaying feature regions of photocleavage produced functional groups; and
   (c) producing by in situ synthesis at least two different polymeric ligands in at least two different feature regions to produce said array;
   wherein said method includes a single photocleavage step that occurs prior to said producing step (c) and wherein said photocleavage produced functional groups are hydroxyl groups.

2. The method according to claim 1, wherein said in situ synthesis method comprises depositing drops of monomeric precursors of said ligands onto said feature regions.

3. The method according to claim 2, wherein said drops are deposited by pulse-jet deposition.

4. A method of producing an array of at least two different ligands covalently bonded to a surface of a substrate, said method comprising:
   (a) contacting a surface of a substrate with at least a first silanizing reagent comprising a photocleavable functional group to produce a surface displaying photocleavable functional groups;
   (b) cleaving said photocleavable functional groups on said surface to produce a patterned surface displaying feature regions of hydroxyl functional groups; and
   (c) producing by in situ synthesis at least two different ligands in at least two different feature regions produced in step (b) to produce said array;
   wherein said method includes a single photocleavage step that occurs prior to said producing step (c).

5. The method according to claim 4, wherein said silanizing reagent comprises terminal silyl and photocleavable groups separated by an alkyl chain.

6. The method according to claim 5, wherein said alkyl chain is from about 2 to about 20 carbon atoms in length.

7. The method according to claim 6, wherein said silanizing reagent has the formula:

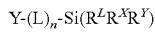

$$Y\text{-}(L)_n\text{-}Si(R^L R^X R^Y)$$

wherein:
   $R^L$ is a leaving group;
   $R^X$ and $R^Y$ are independently lower alkyl or a leaving group;
   L is a $C_2\text{-}C_{20}$ alkyl chain;
   n is 0 or 1; and
   Y is a photocleavable group.

8. The method according to claim 7, wherein said photocleavable group is cleaved when irradiated at a wavelength ranging from about 230 nm to about 700 nm for a period of time ranging from about 0.1 s to about 12 hours.

9. The method according to claim 8, wherein said photocleavable group is chosen from amide, carbonyl, ester, peroxide and aromatic.

10. The method according to claim 9, wherein said photocleavable group is benzoyloxy.

11. The method according to claim 4, wherein said contacting comprises contacting said surface with a second silanizing reagent.

12. The method according to claim 11, wherein said second silanizing reagent has the formula:

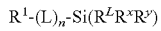

$$R^1\text{-}(L)_n\text{-}Si(R^L R^x R^y)$$

wherein:
   $R^L$ is a leaving group;
   $R^x$ and $R^y$ are independently lower alkyl or a leaving group;
   L is a $C_2\text{-}C_{20}$ alkyl chain;
   n is 0 or 1; and
   $R^1$ is a chemically inert moiety.

13. The method according to claim 4, wherein said method comprises converting said hydroxyl functional group to a reactive functional group.

14. The method according to claim 4, wherein said producing step (c) comprises depositing monomeric ligand precursors onto said surface.

15. The method according to claim 4, wherein said substrate is glass.

16. The method according to claim 4, wherein said ligands are selected from oligonucleotides, polynucleotides, peptide-nucleic acids and peptides.

17. The method according to claim 16, wherein said polynucleotides are deoxyribonucleic acids.

18. The method according to claim 4, wherein said contacting comprises contacting a fluid composition of said silanizing reagent with said substrate.

19. The method according to claim 4, wherein said cleaving step reduces the contact angle of said surface by 30° or more.

20. A method of producing an array of at least two different ligands covalently bonded to a surface of a substrate, said method comprising:
   (a) contacting a surface of a substrate with a mixture of a first silanizing reagent comprising a terminal photocleavable functional group and a second silanizing agent lacking said terminal photocleavable functional group to produce a surface displaying photocleavable functional groups;

(b) cleaving said photocleavable functional groups on said surface to produce a patterned surface displaying feature regions of hydroxyl functional groups; and (c) producing at least two different ligands by in situ synthesis in at least two different feature regions produced in step (b) to produce said array;

wherein said method includes a single photocleavage step that occurs prior to said producing step (c).

* * * * *